United States Patent
Rhodes

(10) Patent No.: US 9,061,145 B2
(45) Date of Patent: Jun. 23, 2015

(54) TECHNIQUE FOR DETERMINING OPTIMUM TREATMENT PARAMETERS

(71) Applicant: Donald A. Rhodes, Corpus Christi, TX (US)

(72) Inventor: Donald A. Rhodes, Corpus Christi, TX (US)

(*) Notice: Subject to any disclaimer, the term of this patent is extended or adjusted under 35 U.S.C. 154(b) by 0 days.

(21) Appl. No.: 13/987,897

(22) Filed: Sep. 13, 2013

(65) Prior Publication Data

US 2015/0080984 A1    Mar. 19, 2015

Related U.S. Application Data

(60) Provisional application No. 61/744,085, filed on Sep. 17, 2012.

(51) Int. Cl.
*A61N 1/36* (2006.01)
(52) U.S. Cl.
CPC .......................................... *A61N 1/36* (2013.01)
(58) Field of Classification Search
CPC ..... A60N 1/323; A60N 1/36; A60N 1/36014; A60N 1/36021; A60N 1/3601
USPC .............................. 607/46, 67, 149–150, 145
See application file for complete search history.

(56) References Cited

U.S. PATENT DOCUMENTS

| | | | |
|---|---|---|---|
| 4,505,275 A | 3/1985 | Chen | |
| 5,211,479 A * | 5/1993 | Coffey et al. | 374/151 |
| 5,995,873 A | 11/1999 | Rhodes | |
| 6,016,447 A | 1/2000 | Juran | |
| 6,154,675 A | 11/2000 | Juran | |
| 6,650,944 B2 * | 11/2003 | Goedeke et al. | 607/60 |
| 6,698,921 B2 | 3/2004 | Siefert | |
| 6,826,429 B2 | 11/2004 | Johnson | |
| 7,329,044 B2 | 2/2008 | Siefert | |
| 2002/0003832 A1 | 1/2002 | Siefert | |
| 2007/0150029 A1 | 6/2007 | Bourget | |
| 2007/0173727 A1 * | 7/2007 | Naghavi et al. | 600/483 |
| 2010/0063564 A1 | 3/2010 | Libbus | |
| 2010/0106226 A1 | 4/2010 | Libbus | |
| 2010/0211135 A1 | 8/2010 | Caparso | |
| 2010/0222844 A1 | 9/2010 | Troosters | |
| 2011/0105916 A1 * | 5/2011 | Rhodes | 600/485 |
| 2011/0106216 A1 | 5/2011 | Libbus | |
| 2011/0152974 A1 | 6/2011 | Reszai | |
| 2011/0238136 A1 | 9/2011 | Boiurget | |
| 2011/0313488 A1 | 12/2011 | Hincapie | |
| 2012/0226197 A1 | 9/2012 | Sanders et al. | |
| 2012/0277621 A1 | 11/2012 | Gerber et al. | |

* cited by examiner

*Primary Examiner* — Paula J Stice
(74) *Attorney, Agent, or Firm* — G. Turner Moller

(57) ABSTRACT

A diagnostic device in an electrical interferential treatment regime applies different pulse frequencies in one selection of electrode placement and determines the change of blood flow in response to the change in pulse frequency in an attempt to determine an optimum or workable set of parameters. The device includes electronic storage to record a series of tests and their results and a communication link. The communication link enables a professional caregiver to determine whether the parameter determinations, made at a location remote from the professional's office, such as at the residence of the patient, were conducted and were conducted correctly. The communication link also enables the professional to determine whether the treatments were conducted and conducted correctly.

15 Claims, 2 Drawing Sheets

TECHNIQUE FOR DETERMINING OPTIMUM TREATMENT PARAMETERS

This application is based on Provisional Application Ser. No. 61/744,085, filed Sep. 17, 2012, priority of which is claimed.

This invention relates to a method and apparatus for determining effective treatment parameters in an electrical interferential system.

BACKGROUND OF THE INVENTION

U.S. patent application Ser. No. 11/374,903, filed Mar. 14, 2006, the disclosure of which is incorporated herein by reference, discloses a technique for determining better treatment parameters for an electrical interferential treatment by delivering various pulses and electrode locations and measuring the patient's response to the applied treatment. By varying these parameters and exercising experienced judgment, an effective set of parameters is obtained for treating the ailment presented by the patient.

Disclosures of some interest relative to this invention are found in U.S. Pat. Nos. 4,505,275; 6,016,447; 6,154,675; 6,698,921 and U.S. Printed Patent Applications 20020003832; 20070150029; 20100063564; 20100106226; 20100211135; 20100222844; 20110105916; 20110106216; 20110152974; 20110231836 and 20110313488.

SUMMARY OF THE INVENTION

In an attempt to obtain more efficient treatment parameters, shorten the time to determine these parameters, require less experienced personnel and rely on patients or their caregivers to determine effective parameters, the responses of the patient may be entered into software designed to obtain better parameters. The software may contain a series of logic circuits which may be briefly described as an effort to determine whether the patient experiences improved blood flow in response to the application of a series of treatment parameters.

One broad manner of intended use of the disclosed technique is for the patient to be initially treated by professionals in a professional setting where a first set of treatment parameters is obtained and a first treatment delivered to the patient. Many subsequent treatments may be conducted by the patient or caregiver at a location other than a professional office, such as at the patient's residence. In order to run subsequent treatments, a new set of treatment parameters may preferably be obtained by the device using the same device and software.

The hardware and software obtain, in an automated way, the patient's response to a series of treatment parameters and saves or stores the patient's responses to the parameters, typically on an electronic storage medium, along with the parameters, the time and manner the parameters were determined and other pertinent information. Similarly, the time and parameters used in a treatment may also be saved or stored. A communications link may be provided to allow a professional to check on whether the treatment parameters were selected in an appropriate manner. Similarly, the communications link may be used to allow a professional to check on whether the treatments were in fact done and done in a manner and at a time consistent with best practice.

BRIEF DESCRIPTION OF THE DRAWINGS

FIG. 3 is a view of a finger tip temperature sensor;

FIG. 4 is a schematic view of one embodiment of a communications link; and

FIG. 5 is a schematic view of another embodiment of the disclosed technique.

DETAILED DESCRIPTION OF THE INVENTION

In the practice of the disclosed technique, electrical energy in the form of electrical interferential pulses are delivered into the patient's body. These treatments cause change in the patient which is monitored by the disclosed device. In other words, the effect of the electrical interferential pulses is monitored by one or more sensors that detect a function or an aspect of the autonomic nervous system. The sensed changes in the patient are then used to modify the output of the treatment unit and/or the placement of the electrodes used by the treatment machine. In other words, the results of the tests are used in an attempt to determine a preferred way to treat the patient by adjusting the treatment machine in response to the tests results.

A healthy organism is capable of quickly adjusting to many external influences because of an adequate sympathetic response. Once that factor disappears, parasympathetic activity increases, which balances overall autonomic activity. It has become known that a large majority of people have overly active sympathetic nervous systems, i.e. their sympathetic nervous systems are overpowering or dominating their parasympathetic nervous system. This may have many effects, some of which may be controversial although many are not. In general, an overly active sympathetic nervous system tends to create or accentuate such diverse conditions or ailments such as diabetes type 1 and type 2, fibromyalgia, bipolar disorder, endometriosis, hypertension and other ailments such as disclosed in application Ser. No. 11/326,230, filed Jan. 5, 2006 or those ailments disclosed in U.S. Pat. No. 5,995,873.

A wide variety of techniques may be used to monitor the autonomic nervous system and thereby determine the effect of an interferential treatment on the patient. A preferred technique is to monitor finger tip temperature because the response is relatively rapid, easy to measure and is relatively unambiguous. In the alternative, or in addition, to monitoring finger tip temperature, other manifestations of the autonomic nervous system may be monitored, for example, skin resistivity, pulse rate, blood pressure, iris pupil diameter, respiration rate, or any other indicator of autonomic nervous system function.

Figure 1:
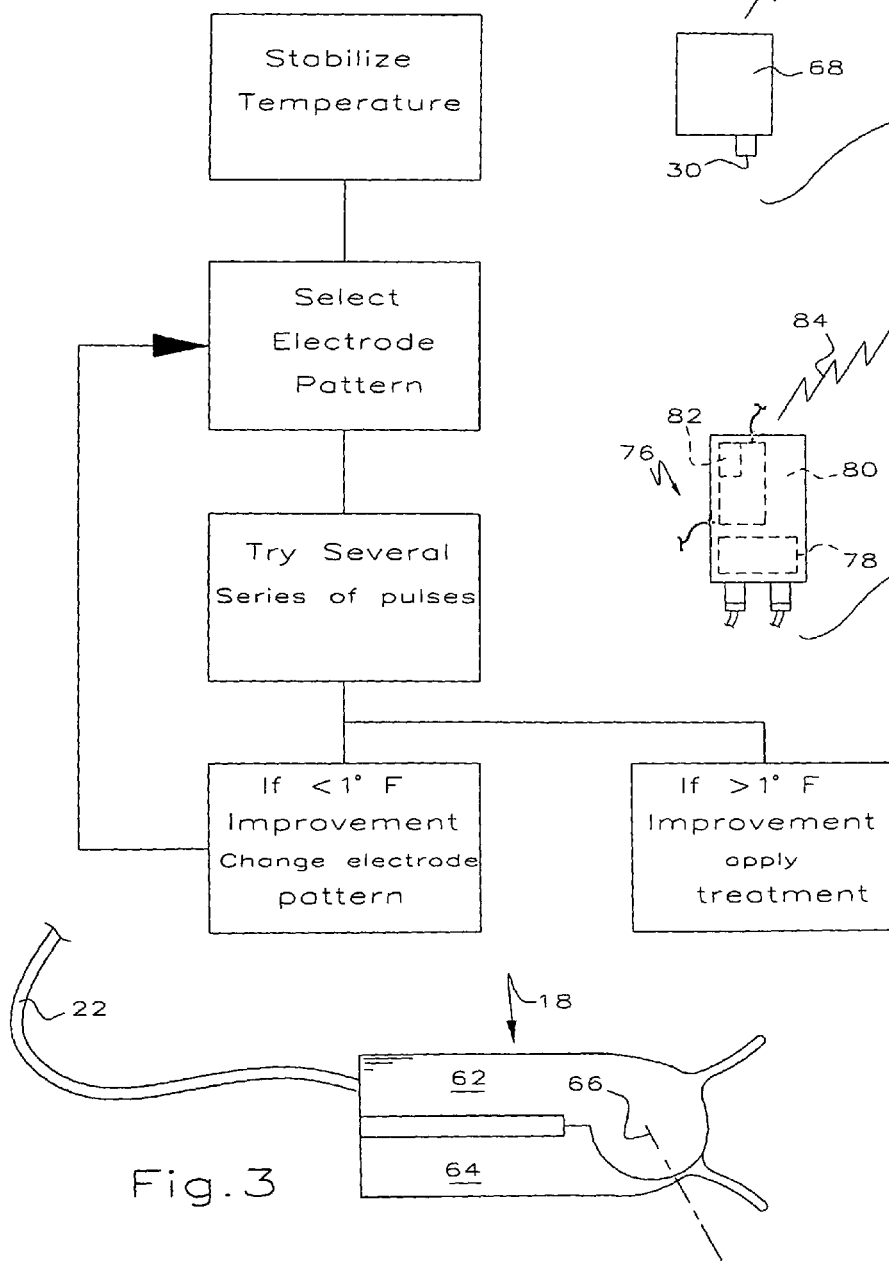
FIG. 1 is a flow chart of an automated parameter selection technique.
Figure 2:
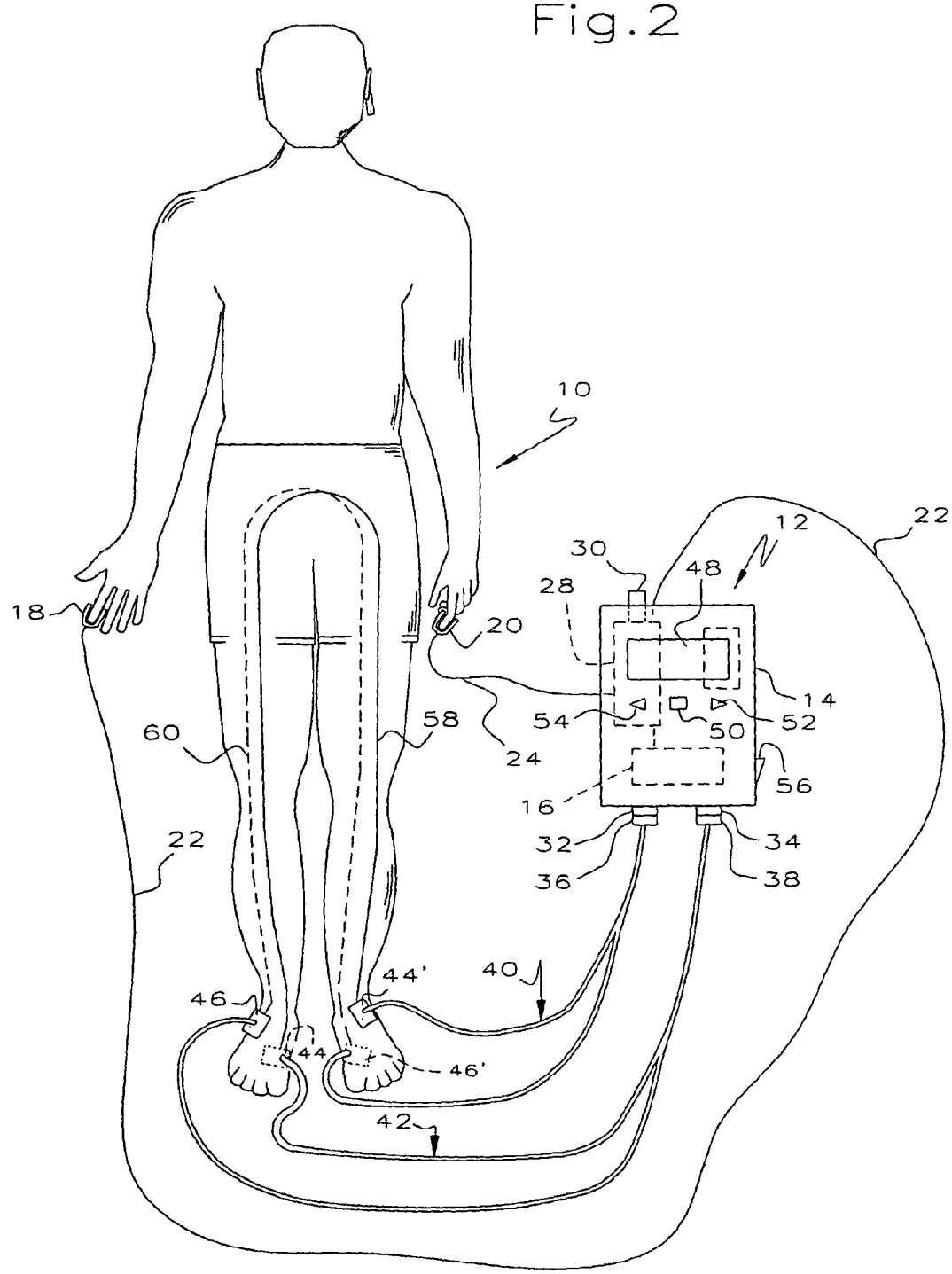
FIG. 2 is a combined schematic view of a diagnostic system and a pictorial view of the application of electrodes to a patient in accordance.

Referring to FIGS. 1-2, a patient 10 is hooked up to an electrical interferential therapy device 12 inside a housing 14. The electrical interferential therapy device 12 may include a more-or-less conventional treatment module 16 such as is commercially available from Dynatronics, Inc. of Salt Lake City, Utah, to which reference is made for a more complete description thereof and as explained more fully hereinafter. The reaction of the patient 10 is monitored by one or more sensors 18, 20 which may preferably be a digital temperature sensor incorporated into a spring biased clip which may attach to a finger or toe on each side of the patient. Each sensor 18, 20 may be connected by a wire 22, 24 to a module 28 in the housing 14. The module 28 may be a data processor to record the temperature sensings from the sensors 18, 20, store the values in a memory module 30, control the treatment module 16 and otherwise operate the device 12. In some embodiments, the memory module 30 may be removable from the housing 14 for purposes more fully explained hereinafter.

The housing 14 may include a pair of receptacles 32, 34 capable of accepting a jack 36, 38 of insulated wire pairs 40, 42 leading to electrode pairs 44, 44' and 46, 46'. A suitable display 48 provides readings such as values from the sensors 18, 20, the carrier frequency, the pulse frequency being tested, the time and date of the procedure and any other desirable information, such as the intensity of treatment, time left to finish the treatment, time elapsed during a particular testing cycle, results of testing sequences, and whether it is time to replace the electrodes.

Standard commercially available electrical interference treatment devices have either a fixed carrier frequency or a minimally selective carrier frequency. For reasons which are mainly historical, these frequencies are conventionally 1850 Hz and 2850 Hz in the Sympathetic Therapy System from Dynatronics, Inc. and 4000 Hz in a device commercially available by Rehabilicare Corporation of St. Paul, Minn. In this device, the carrier frequency may be either fixed or variable.

The device 12 may include a select actuator 50 and up/down actuators 52, 54. It is sometimes desirable to increase the intensity of the electrical pulses. Assuming the actuator 52 to increase intensity, it may be manually depressed and an intensity value may be displayed on the screen 48. When the desired intensity value shows on the screen 48, the select actuator 50 may be depressed to instruct the module 28 to increase the intensity to the selected value. The module 28 may provide other functions. For example, the electrodes 44, 44', 46, 46' don't provide good sensings indefinitely. The module 28 may run tests to determine whether the electrodes need to be replaced, may count the number of treatments or the number of parameter determining trials are run and display a message on the screen 48 to replace the electrodes. In response to such a message, the select actuator 50 may be depressed to send a message to the module 28 that the electrodes have been or will be changed. The device 12 may also include a timer function and the time of and duration of treatments and/or the acquisition of treatment parameters. The device 12 may also include an on-off switch 56.

The carrier and beat frequencies used in selecting treatment parameters may be selected by the actuators 50, 52, 54 or default selections may be provided by software in the processor 28. Experience has shown that the vast majority of desirable beat frequencies are between 1-150 beats per second (bps) although current commercially available devices only employ 1-80 beats per second. In attempts to find the most desirable beat frequency in a reasonable time frame, this range has been subdivided into smaller segments. Experience has shown that some of the segments, at least at one carrier frequency where most efforts have been made, provide the most desirable beat frequency.

When it is desired to increase the treatment intensity, the increase actuator 52 is depressed. When it is desired to decrease the treatment intensity, the decrease actuator 54 is depressed. It will accordingly be seen that the device 12 includes a circuit for delivering therapeutic electrical energy into the body of the patient and more particularly includes a subcircuit for modifying the carrier frequency, the beat frequency and/or the amplitude of alternating current type energy.

The first thing that may be done is to allow or insure that the finger tip temperature of the patient has stabilized. The patient's finger temperatures often change in response to room temperature and it may be desirable to allow them to cease responding to room temperature. This may be done by measuring the initial temperature of the patient's finger tips and determining whether the temperature is varying over time. At the end of a short specified period, e.g. one minute, a determination is made whether finger tip temperature has stabilized by comparing initial and subsequent temperatures. A suitable set of parameters is that when finger tip temperature changes less than 1° F. in one minute, the processor 28 determines that temperature has stabilized and the acquisition of treatment parameters continues in accordance with FIG. 1.

The electrodes are attached to the patient's skin in a conventional manner, i.e. they may be self adherent. The location of the electrodes on the patient establish the electrical circuit in the patient's body. As shown in FIG. 2, in one technique, one electrode 44 is placed adjacent the end or terminus of the right medial plantar nerve L5 and its matching electrode or mate 44' is placed adjacent the end or terminus of the left sural nerve S1, inferior to the left ankle bone (lateral malleolus) thereby establishing or creating a first circuit 58 in the patient's body. As used herein, the reference characters L5, S1 and the like are standard medical terminology for the nerve. Those skilled in the art will recognize L5 as being the nerve which extends away from the fifth lumbar vertebra and S1 as being the nerve which extends away from the first sacral vertebra.

The electrode pattern illustrated in FIG. 2 and as described is shown in U.S. Pat. No. 5,995,873. It will be understood that there are hundreds or thousands of potential electrode patterns. In addition to the L5-S1 pattern described above, a preferred approach may be to employ an additional four electrodes for a total of eight electrodes. The additional electrodes may be placed in any suitable manner, such as in a L4-S2, L5-L4 pattern or in acupuncture sites on the feet.

Those skilled in the art will recognize that the terminus of the right medial plantar nerve L5 is located on the bottom of the right foot, approximately on the ball of the foot. The terminus of the left sural nerve S1 is located below the left ankle bone (lateral malleolus). Another electrode 46 is placed adjacent the terminus of the right sural nerve S1 and its matching electrode or mate 46' is placed adjacent the terminus of the left medial plantar nerve L5 thereby establishing a second circuit 60 in the patient's body. Turning the device 12 on delivers electrical energy through the circuits 58, 60. Those skilled in the art will recognize that the medial plantar nerves L5 and the sural nerves S1 terminate adjacent the spinal column near adjacent spinal vertebra, in the area of the connection to the lumbar sympathetic ganglia.

Other arrangements of the electrodes to stimulate other nerves are within the scope of this invention and are shown in U.S. Pat. No. 5,995,873. There are several thousand potential electrode arrangements so it is desirable to start the acquisition of treatment parameters by selecting one arrangement that experience has shown to often produce effective treatments.

Referring to FIG. 3, there is illustrated a suitable temperature sensor 18 of a type available from Minnesota Wire Company of Saint Paul, Minn. The sensor 18 may include a pair of clip sections 62, 64 connected for pivotal movement about an axis 66. A spring (not shown) biases the sections 62, 64 together. An infrared temperature sensor (not shown) or other suitable temperature measuring device is incorporated into one or the other of the clip sections 62, 64. In the alternative, an infrared sensor (not shown) may be exposed on the housing 14 so the patient simply places finger tips on the housing 14.

Initially, the patient is briefly subjected to no carrier frequency or frequencies or beat frequency or frequencies for a short period, typically about five minutes, in order to allow the thermistors to equilibrate to the finger temperature. Then, the patient is subjected to a series of tests, initially using different beat frequencies in an attempt to determine an effective, optimum or ideal combination of parameters that produce a desired effect on the autonomic nervous system and thereby determine a preferred treatment regimen. This may be accomplished by using one of the carrier frequencies and delivering a series of pulses in a first range, such as 1-10 pulses/second, while sensing and recording the temperature measured by the sensors 18, 20. The sequence of delivering the pulses may be in any suitable manner. The standard interferential module 16 produces a sweep of beats in this range in the following repeating pattern: 1, 2, 3, 4, 5, 6, 7, 8, 9, 10, 10, 9, 8, 7, 6, 5, 4, 3, 2, 1, changing every second. The finger tip temperature may be recorded continuously or at any suitable interval, e.g. one minute. A hypothetical temperature pattern conducted on a female having an original left finger tip temperature of 71.2° F. and an original right finger tip temperature of 72.6° F. is shown in Table I:

TABLE I

|  | left finger | right finger | average |
|---|---|---|---|
| initial | 71.2 F. | 72.6 F. | 71.9 F. |
| end of 1 min | 71.6 F. | 72.8 F. | 72.2 F. |
| end of 2 min | 71.6 F. | 72.8 F. | 72.2 F. |
| end of 3 min | 71.6 F. | 72.6 F. | 72.1 F. |

The purpose of the trial is to determine parameters that produce a significant increase in digit temperature based on the premise that this is a proxy for improved blood circulation. Table I shows a situation where the subject's finger tip temperature increased about 0.4° F. in three minutes. This suggests a minimal increase in blood circulation so software in the processor module 28 concludes the selected pulse beat frequency and electrode placement is ineffective.

The module 28 accordingly writes onto the memory module 30 information relevant to the trial, e.g. the serial number of the device 12, the time and date of the trial, and all of the data created during the testing and running of the treatment onto the memory module 30.

If the temperature response from the first trial is not satisfactory, as in Table I, which may be where the digit temperature increase is less than 1° F., then a second trial may commence using a different pulse frequency, e.g. 11-20 beats per second. This process repeats until a temperature increase above some minimum, which is preferably at least 1° F. in a few minutes such as three or four minutes, is attained or until some maximum range is reached. If there is no successful trial after trying each ten pulse range through the maximum range, a message appears on the display 48 to try a different electrode pattern and/or a different carrier frequency. The process is repeated until a satisfactory temperature increase is obtained. All of the trial parameters and trial results are written onto the memory module 30.

Following a successful trial that determines parameters suggesting substantially improved blood flow, i.e. the temperature response is above a predetermined threshold such as a 1° F. temperature rise in a few minutes, the selected treatment may be delivered to the patient in response to a message on the display 48 or automatically. The patient, caregiver or professional may instruct the device 12 to apply the treatment by depressing the select actuator 50. If, having tested all of the beat frequency permutations available, no combination is able to create an adequate thermistor temperature increase indicating an adequate circulation increase, the beat frequency combination which created the highest increase will be utilized for the treatment. At the end of the treatment, a message appears on the display 48 saying "new protocol needed" or other similar message advising the clinician or patient that a different electrode placement is needed. In the alternative, in a situation where the patient or caregiver is conducting these trials at a location remote from the professional's premises, the message may indicate that the professional be contacted to determine another electrode pattern or that a reference book or data base be used to determine another electrode pattern.

The memory module 30 provides an important advantage. There are situations where the patient or patient's caregiver is conducting trials to determine suitable parameters and then delivering treatments at a location away from the professional's office, e.g. at the patient's residence. In this situation, it is very desirable to have the capability of reviewing the trial procedures and results. In the case of a removable memory module, the module 30 may be removed and placed in a computer 68 where data from the module 30 may be transmitted through a communication link 70 to the professional's office 72 where the data can be stored on a computer 74, retrieved and viewed (FIG. 4). In this manner, the professional can determine from a location remote from the patient whether the parameter determining trials were run and run correctly. Manifestly, if the parameter determining trials are run incorrectly or not run at all, this can be determined by the professional and appropriate steps taken to correctly determine parameters. It is difficult to overstate the importance of this advantage. It will be apparent that the communication link 70 may be of any suitable type, such as by an Internet connection.

The communication link 70 also allows the professional to review whether, when and how treatments were conducted because treatment information, as well as parameter acquisition information, is written onto and stored on the memory module 30. Thus, treatment information as well as parameter information may be transmitted to the professional.

Referring to FIG. 5, there is illustrated another embodiment of an interferential device 76 including an interferential treatment module 78 and a processor module 80 which includes all of the functions of the processor 28 and a communication module 82 providing a communication link 84 directly with a computer 86 in a professional's office 88. The communication link 84 may be of any suitable type, such as a cell phone, Internet connection or the like. It will be seen that the interferential device 76 transmits parameter determining information as well as treatment information to the computer 86 so it may be reviewed for accuracy and timeliness.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A method to facilitate home use including determining and applying treatment parameters for an electrical interferential treatment regimen conducted on a patient residing at a first location, comprising externally applying pairs of electrodes, respectively, at selected placements to opposite limbs of a patient situated at said first location and delivering a series of trial electrical interferential treatments to the patient produced by at least one electronic device at said first location through the electrodes, and, for a pair of electrode placements, each electrical interferential treatment comprises electrical interferential treatment parameters of at least one beat frequency;

measuring at least one biological function responsive to autonomic nervous system activity of the patient caused by each electrical interferential treatment parameter delivered and calculating a numerical value indicative of the at least one measured biological function for each treatment parameter delivered;

comparing each said numerical value to a predetermined numerical value indicative of a desired biological function;

determining whether each said numerical value is in excess of said predetermined numerical value and identifying at least one of said electrical interferential treatment parameters that produced a numerical value in excess of said predetermined numerical value;

storing data, in said at least one electronic device, of said numerical values, said treatment parameters of said series of trial electrical interferential treatments and said treatment parameters of said at least one identified electrical interferential treatment;

electronically transmitting said stored data to at least one other electronic device situated at a second location away from the immediate vicinity of the first location, selecting from said stored data said treatment parameters of said identified electrical interferential treatment that produced said numerical value in excess of the predetermined value and applying the selected parameters through the electrodes to the patient in a subsequent selected treatment regimen; and viewing, at said first and second locations, said stored data of said numerical values, said treatment parameters of said series of trial electrical interferential treatments and said treatment parameters of said identified electrical interferential treatment that produced said numerical value in excess of the predetermined value and determining from said stored data whether said treatment parameters of said identified electrical interferential treatment produced a numerical value in excess of the predetermined value.

2. The method of claim 1 wherein the first location comprises a residence of the patient and the second location comprises a professional office.

3. The method of claim 1 wherein the step of storing data further includes storing the time and date of the application of each said series of trial treatment parameters and said treatment parameters of said identified electrical interferential treatment that produced said numerical value in excess of the predetermined value.

4. The method of claim 3 wherein the step of electronically transmitting transmits said stored data and time and date of said series of trial treatment parameters and said treatment parameters of said identified electrical interferential treatment that produced said numerical value in excess of the predetermined value to said at least one electronic device and to said at least one other electronic device; whereby said stored data corresponding to said numerical value that is in excess of said predetermined value is viewed at both said electronic devices for determining from said stored data whether said treatment parameters of said identified electrical interferential treatment produced said numerical value in excess of the predetermined value.

5. The method of claim 4 wherein the first location comprises a residence of the patient and the second location comprises a professional office.

6. The method of claim 1 wherein the step of measuring of at least one biological function comprises measuring finger temperature.

7. The method of claim 6 further comprising determining whether the applied selected treatment parameters produce at least a one degree Fahrenheit increase in finger temperature in less than four minutes thereby constituting an effective treatment regimen.

8. The method of claim 6 further comprising equalizing the patient's initial finger temperature to ambient temperature by measuring the patient's finger temperature prior to delivering the series of trial electrical interferential treatments and, when the rate of change of finger temperature falls below a predetermined value, commencing delivering the series of trial electrical interferential treatments through the electrodes.

9. The method of claim 8 wherein the predetermined value of the rate of change is at least one degree Fahrenheit per minute.

10. A system configured for use including determining and applying treatment parameters for an electrical interferential treatment regimen conducted on a patient situated at a first location, comprising:

pairs of electrodes adapted for external temporary attachment, respectively, to opposite limbs of a patient situated at said first location and at least one electronic device at said first location for delivering a series of trial electrical interferential treatments to the patient through the electrodes, and, for a pair of electrode placements, each electrical interferential treatment comprises electrical interferential treatment parameters of at least one beat frequency;

a sensor configured to measure at least one biological function responsive to autonomic nervous system activity of the patient caused by each electrical interferential treatment parameter delivered;

said at least one electronic device responsive to said sensor and adapted to calculate a numerical value indicative of the at least one measured biological function;

said at least one electronic device further adapted to compare said numerical value to a predetermined numerical value indicative of a desired biological function;

said at least one electronic device further adapted to determine whether said numerical value is in excess of said predetermined numerical value;

said at least one electronic device further adapted to store data of said numerical values, said treatment parameters of said series of trial electrical interferential treatments and said treatment parameters of said at least one electrical interferential treatment that corresponds to a numerical value that is in excess of said predetermined numerical value;

said at least one electronic device further adapted to electronically transmit said stored data of said numerical values, said treatment parameters of said series of trial electrical interferential treatments and said treatment parameters of said at least one electrical interferential treatment that corresponds to a numerical value that is in excess of said predetermined numerical value to at least one other electronic device situated at a second location away from the immediate vicinity of the first location;

said at least one electronic device further adapted to select said treatment parameters of the at least one electrical interferential treatment that produced said numerical value in excess of the predetermined value and apply the selected treatment parameters through the electrodes to the patient in a subsequent selected treatment regimen; and said at least one electronic device and said at least one other electronic device are adapted for viewing said numerical values, said treatment parameters of said series of trial electrical interferential treatments and said treatment parameters of said identified electrical interferential treatment that produced said numerical value in excess of the predetermined value and determining from said stored data whether said treatment parameters of said identified electrical interferential treatment produced a numerical value in excess of the predetermined value.

11. The system of claim 10 wherein said first location comprises a residence of the patient and the second location comprises a professional office.

12. The system of claim 10 wherein the sensor comprises a finger temperature sensor.

13. The system of claim 12 wherein said finger temperature sensor is adapted to measure a patient's finger temperature prior to delivering the series of trial electrical interferential treatments and, said at least one electronic device, in response to a measured rate of change of finger temperature falling below a predetermined value, is adapted to deliver said series of trial electrical interferential treatment parameters through the electrodes.

14. The system of claim 13 wherein the predetermined value of said rate of change is at least one degree Fahrenheit per minute.

15. The system of claim 14 wherein the first location comprises a residence of the patient and the second location comprises a professional office.

* * * * *